US007179798B2

(12) United States Patent
Roby

(10) Patent No.: US 7,179,798 B2
(45) Date of Patent: Feb. 20, 2007

(54) METHODS AND COMPOSITIONS FOR THE TREATMENT OF PAIN AND OTHER HORMONE-ALLERGY-RELATED SYMPTOMS USING DILUTE HORMONE SOLUTIONS

(75) Inventor: Russell R. Roby, 3410 Far West Blvd., Suite 110, Austin, TX (US) 78731

(73) Assignee: Russell R. Roby, Austin, TX (US)

( * ) Notice: Subject to any disclaimer, the term of this patent is extended or adjusted under 35 U.S.C. 154(b) by 239 days.

(21) Appl. No.: 10/294,512

(22) Filed: Nov. 14, 2002

(65) Prior Publication Data
US 2003/0096801 A1 May 22, 2003

Related U.S. Application Data

(60) Provisional application No. 60/332,475, filed on Nov. 16, 2001.

(51) Int. Cl.
*A61K 31/56* (2006.01)
(52) U.S. Cl. ...................................... 514/169; 514/170
(58) Field of Classification Search ................ 514/169
See application file for complete search history.

(56) References Cited

U.S. PATENT DOCUMENTS

| 4,596,795 | A | * | 6/1986 | Pitha ............................ 514/58 |
| 5,108,995 | A | | 4/1992 | Casper ....................... 514/170 |
| 5,504,074 | A | | 4/1996 | D'Amato et al. ........... 514/182 |
| 5,744,463 | A | | 4/1998 | Bair ............................ 514/177 |
| 5,855,920 | A | | 1/1999 | Chein ......................... 424/568 |
| 6,207,646 | B1 | | 3/2001 | Krieg et al. .................. 514/44 |

FOREIGN PATENT DOCUMENTS

| WO | 97/45125 | 12/1997 |
| WO | 98/29122 | 7/1998 |

OTHER PUBLICATIONS

Quirino et al. Sublingual versus injective immunotherapy in grass pollen allergic patients: a double blind (double dummy) study. Clinical Experimental Allergy, vol. 26 pp. 1253-1261, 1996.*
English et al. Low-dose transdermal testosterone therapy improves angina thrshold in men with chronic stable angina:A randomized, double-blind, placebo-controlled study. Circulation, (Oct. 17, 2000) 102(16) pp. 1906-1911.*
O'Neil, John, "Preventing Women's Migraines", The New York Times, Section F, p. 6, Jul. 27, 2004.
Passalacqua, et al., "Efficacy and Safety of Sublingual Immunotherapy", Annals of Allergy, Asthma & Immunology, 93:3-12, Jul. 12, 2004.
International Search Report with Notification of Transmittal, PCT/US02/37105; 6 pages, mailed Sep. 12, 2003.
Mabry et al., "Treatment of Common Gynecologic-Endocrinologic Symptoms by Allergy Management Procedures;" Allergy Management of Common Symptoms; vol. 59, No. 5, May 1982.

Joseph B. Miller, "Relief of Premenstrual Symptoms, Dysmenorrhea, and Contraceptive Tablet Intolerance, Journal of the Medical Association of the State of Alabama, " vol. 44, No. 2 Aug. 1974.
Dr. Farida A. Talati, "Effects of Potentised Oestrogen & Progesteron on Dysmenorrhoea", Indian Journal of Homeopathic Medicine, p. 175, Apr.-Jun. 1990.
Supplementary European Search Report for Application No. EP 02782324, 2 pages, Feb. 24, 2005.
Rainer Rupprechta et al.'s, "Neuropsychopharmacological properties of neuroactive steroids", Steriods: Structure, Function, and Regulation, Elsevier Science Publishers, New York, NY, vol. 64, No. 1-2, pp. 83-91, Jan. 2, 1999.
International Search Report and Written Opinion PCT/US05/13321, 12 Pgs, Nov. 15, 2005.
Kristin K. Snow et al., "Association Between Reproductive and Hormonal Factors and Age-related Maculopathy in Postmenopausal Women", American Journal of Ophthalmology, vol. 134, No. 6, pp. 842-848, Dec. 2002.
www.nei.nih.gov; "Age Related Macular Degeneration: What You Should Know"; National Eye Institute; p. 15, Jan. 6, 2004.
John O'Neil; "Vital Signs: Patterns; Preventing Women's Migraines"; New York Times, Section F; p. 2, Jul. 27, 2004.
A. Zorgdrager et al.; "The Premenstrual Period and Exacerbations in Multiple Sclerosis"; European Neurology; vol. 48; pp. 204-206, 2002.
T. Mennini et al.; "Tianeptine, A Selective Enhancer of Serotonin Uptake in Rat Brain"; Naunyn-Schmiedeberg's Archives of Pharmacology, vol. 336; pp. 478-482, 1987.
M. Rehavi et al.; "Upregulation of Imipramine binding and Serotonin Uptake by Estradiol in Female Rat Brain"; Brain research, vol. 410, pp. 135-139, 1987.
M.J. Owens et al.; "Role of Serotonin in the Pathophysiology of Depression: Focus on the Serotonin Transporter"; Clinical Chemistry, vol. 40, No. 2; pp. 288-295, 1994.
J.K. McQueen et al.; "Estradiol-17β Increases Serotonin Transport (SERT) mRNA Levels and the Density of SERT-binding Sites in Female Rat Brain"; Molcular Brain Research, vol. 45; pp. 13-23, 1997.
J.K. McQueen et al.; "Oestradiol-17β Increases Serotonin Transporter (SERT) Binding Sites and SERT mRNA Expression in Discrete Regions of Female Rat Brain"; The Journal of Physiology, vol. 495, p. 2, 1996.

(Continued)

*Primary Examiner*—Sreenivasan Padmanabhan
*Assistant Examiner*—Jennifer Kim
(74) *Attorney, Agent, or Firm*—Baker Botts L.L.P.

(57) ABSTRACT

A method and composition for the treatment of hormone allergy is disclosed. The method relates to using progesterone dilutions, or any other steroid hormone, to treat the systemic symptoms of hormone allergy, including pain. The composition of the hormone dilutions ranges from $10^{-1}$ to $10^{-5}$. The hormone dilution may be administered sublingually, or, in the alternative, an intradermal route of administration may be chosen. Hormone dilutions may be administered at daily intervals or on any other treatment schedule as required to alleviate a patient's symptoms.

2 Claims, 1 Drawing Sheet

OTHER PUBLICATIONS

A.D. Ogilvie et al.; "Polymorphism in Serotonin Transporter Gene Associated With Susceptibility to Major Depression"; The Lancet, vol. 347; pp. 731-733, Mar. 16, 1996.

S. Ramamoorthy et al.; "Antidepressant- and Cocaine-Sensitive Human Serotonin Transporter: Molecular Cloning, Expression, and Chromosomal Localization"; Proceedings of the National Academy of Science USA, vol. 90, pp. 2542-2546, 1993.

S. Ramamoorthy et al.; "Regulation of the Human Serotonin Transporter"; The Journal of Biological Chemistry, vol. 268, No. 29; pp. 21626-21631, 1993.

I.M. Anderson et al.; "The Efficacy of Selective Serotonin Re-Uptake Inhibitors in Derpression: A Meta-Analysis of Studies Against Tricyclic Antidepressants"; Journal of Psychopharmacology, vol. 8, No. 4; pp. 238-249, 1994.

R. Roby et al.; "Hormone Allergy"; American Journal of Reproductive Immunology; vol. 55, Issue 4; pp. 307-313, 2006.

Frankfurt et al.; "Effect of 5,7-Dihydroxy-Tryptamine, Ovariectomy and Gonadal Steroids on Serotonin Receptor Binding in Rat Brain"; Neuroendocrinology, vol. 59; pp. 245-250, 1994.

A. Weizman et al.; "Platelet Serotonin Transporter in drug-Naive Migrainous Children and Adolescents"; Biological Psychiatry, vol. 35; pp. 452-456, 1994.

S. Mendelson et al.; "Autoradiographic Analyses of the Effects of Estradiol Benzoate on [$^3$H]paroxetine Binding in the Cerebral Cortex and Dorsal Hippocampus of Gonadectomized Male and Female Rats"; Brain Research, vol. 601; pp. 299-302, 1993.

J.L. Snyder et al.;"Autoimmune Progesterone Dermatitis and Its Manifestation as Anaphylaxis: A Case Report and Literature Review"; Annals of Allergy, Asthma & Immunology, vol. 90; pp. 469-477, 2003.

E.A. MacGregor et al.; "Prevalance of Migraine on Each Day of the Natural Menstrual Cycle"; Neurology, vol. 63; pp. 351-353, 2004.

C.L. Haggerty et al.; "The Impact of Estrogen and Progesterone on Asthma"; Annals of Allergy, Asthma, & Immunology, vol. 90; pp. 284-291, 2003.

L. Rees; "An Aetiological Study of Premenstrual Astma"; Journal of Psychosomatic Research, vol. 7; pp. 191-197, 1963.

O. Eliasson et al.; "Morbidity in Asthma in Relation to the Menstrual Cycle"; J. Allergy Cli. Immunol., vol. 77, No. 1; pp. 87-94, 1986.

C.J. Gibbs et al.; "Premenstrual Exacerbation of Asthma"; Thorax, vol. 39; pp. 833-836, 1984.

N.L. Wulfsohn et al.; "Bronchial Asthma During Menses and Pregnancy"; S. African Med. J., vol. 38; p. 173, 1964.

M.H.H. Chandler et al.; "Premenstrual Asthma; The Effect of Estrogen on Symptoms, Pulmonary Function, and $\beta$2-Receptors"; Phamacotherapy, vol. 17, No. 2; pp. 224-234, 1997.

E.M. Skobeloff et al.; "The Effects of the Menstrual Cycle on Asthma Presentations in the Emergency Department"; Arch. Intern. Med., vol. 156; pp. 1837-1840, Sep. 9, 1996.

E.J. Calabrese et al.; "Hormesis as a Biological Hypothesis"; Environmental Health Perspectives 106, Supplement 1; p. 17, 1998.

* cited by examiner

METHODS AND COMPOSITIONS FOR THE TREATMENT OF PAIN AND OTHER HORMONE-ALLERGY-RELATED SYMPTOMS USING DILUTE HORMONE SOLUTIONS

RELATED APPLICATION

This application claims the benefit, under 35 U.S.C. § 119(e), of previously filed provisional application Methods And Compositions For The Treatment Of Allergy Using Dilute Hormone Solutions, Ser. No. 60/332,475, filed Nov. 16, 2001.

TECHNICAL FIELD

The present invention relates in general to the treatment of pain and other hormone-allergy-related symptoms and in specific to the use of a dilute hormone solution for the treatment of pain and hormone-allergy symptoms.

BACKGROUND OF THE INVENTION

Hormone allergy has been previously described in the medical literature as premenstrual asthma. Skobeloff E. M., Spivey W. H., Silverman R. A., Ekin B. A., Harchelroad F. P., Alessi T. V.: The effect of the menstrual cycle on asthma presentations in the emergency department. *Arch Intern Med* 1996; 156: 1837–40. Claude F.: Asthma et menstruation. *Presse Med* 1938; 46: 755–759; Eliasson O., Scherzer H., DeGraff A. C.: Morbidity in asthma in relation to the menstrual cycle. *J Allergy Clin Immunol* 1986: 77: 87–94; Chandler M. H., Schuldheisz S., Phillips B., Muse K. N.: Pre-menstrual asthma: the effect of estrogen on symptoms, pulmonary function, and beta 2-receptors. *Pharmacology* 1997; 17(2): 224–234.

Premenstrual asthma is a condition where premenstrual fluctuations in hormones such as estrogen and progesterone cause the exacerbation of clinical symptoms. Exacerbations of symptoms appear to occur during the premenstrual period when progesterone levels are high. Several references have been made to a possible reaction to hormones. The first report of hormonal influence on asthma symptoms appeared in a case report by Frank from 1931. Frank, R T: The hormonal causes of pre-menstrual tension. *Arch Neurol Psychiatry* 1931; 26: 1053–57. Severe aggravation of asthma symptoms in one patient were clearly linked to oral contraceptives. Derimov, GS, Oppenheimer J: Exacerbation of premenstrual asthma caused by an oral contraceptive. *Ann Allergy Asthma Immunol* 1998; 81: 243–46.

Skobeloff et. al reported a four-fold increase in the presentation of asthmatic women to the emergency department during the perimenstrual interval (days 26 to 04 of the menstrual cycle). When Skobeloff's data is superimposed over the hormone levels during the menstrual cycle, it shows that the peak emergency room visits occurred during the premenstrual period when the progesterone is highest relative to estrogen (FIG. 1).

There has been little investigation, however, into the systemic manifestations or treatment of hormone allergy, or the effect of hormones on organ systems other than the female reproductive tract. While there is documentation in the literature supporting the influence of hormones on pre-menstrual asthma, applicant knows of no established mode of action.

SUMMARY OF THE INVENTION

In accordance with teachings of the present invention, a method and composition for treatment of hormone allergy using steroid hormone dilutions, specifically progesterone, estrogen and testosterone is provided.

Observations that lead to and are a part of the present invention, suggest the possibility of an allergic reaction to the steroid hormone progesterone as a possible cause of clinical symptoms or premenstrual asthma and other disorders.

One aspect of the present invention includes a previously unrecognized treatment for asthma, headache, sinus congestion, muscular pain, and bone and joint pain that involves desensitizing a body's response to its own innate hormones. The treatment may be applied to any mammal including humans. In an exemplary embodiment, the mammal is female.

While hormones may fluctuate throughout the menstrual cycle, treatment is not limited to any specific point in the menstrual cycle. In an exemplary embodiment, however, dilute solutions of progesterone are administered sublingually, every day or every other day, as needed, until there is an alleviation of a patient's clinical symptoms. These dilute formulations are very similar to the type of dilutions that an allergist typically uses when treating allergic symptoms from external substances, or allergens, which are foreign to the body. However, in treating a patient with hormone allergy, instead of desensitizing the patient to a foreign substance, the patient is desensitized to his or her own innate hormone(s).

Existing clinical treatments do not generally use sublingual administration of dilute hormone solutions to treat allergy symptoms. In addition, many of the symptoms that can be treated with hormone dilutions are not recognized as conventional allergy symptoms, such as bone and joint pain, muscular pain, and headache. Other symptoms which respond to treatment with hormone dilutions are recognized as classic allergy symptoms such as sinus congestion, ear and throat pain, eye and skin irritation.

In accordance with another aspect of the present invention, dilutions of a hormone solution, such as progesterone are used to treat hormone allergy symptoms. A hormone dilution ranging in concentration from 5 mg/ml to 0.5 µg/ml is administered sublingually. The strength of the dilution selected for treatment may be based on the severity of the patient's symptoms and prior treatment history. The amount, frequency and strength of the hormone dilution may be varied depending on severity of symptoms and on response achieved.

In an alternative embodiment of the invention, the route of administration may be intradermal.

In accordance with a further aspect of this invention a dilute progesterone solution (concentration 5 mg/ml to 0.5 µg/ml) or a dilute estrogen solution (concentration 5 mg/ml to 0.5 µg/ml) may be administered to treat hormone allergy symptoms in females.

In accordance with another aspect of this invention a dilute testosterone solution (concentration 5 mg/ml to 0.5 µg/ml) may be used to treat allergy symptoms in males. Other steroid hormone solutions may also be used. All solutions of the present invention may be administered in a pharmaceutically-acceptable carrier.

BRIEF DESCRIPTION OF THE DRAWINGS

A more complete and thorough understanding of the present invention and advantages thereof may be acquired by referring to the following description taken in conjunction with the accompanying drawings, in which like reference numbers indicate like features, and wherein.

DETAILED DESCRIPTION OF THE INVENTION

Figure 1:
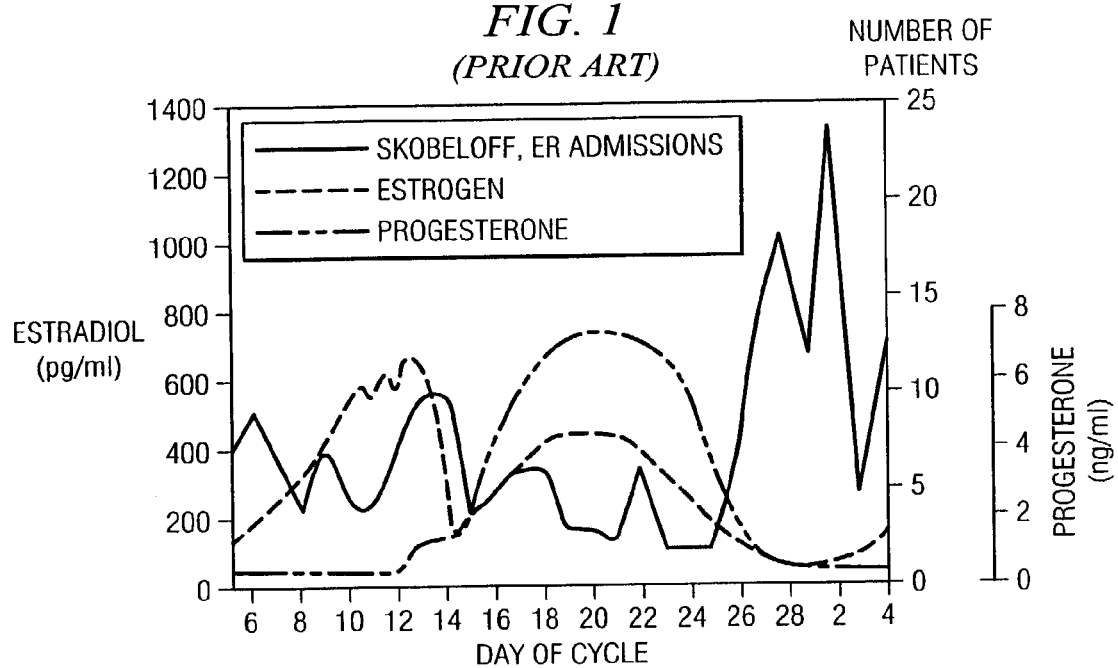
FIG. 1 illustrates the number of female asthmatic patient visits to an emergency department during the menstrual cycle.

The present invention relates to a treatment of systemic allergic manifestations and pain caused at least in part by steroid hormones. Such manifestations have been observed and treated in female patients. For the condition of acute asthma alone, data on 83 patients treated with dilute progesterone has been collected. Measuring symptom response rate on a 10-point scale, a response rate of 93% overall was observed. The average reduction in symptom severity on the 10-point scale was 3.1 points. The present data show a 57% reduction in symptoms on average. These results are statistically significant at a level of $p<0.0001$.

A composition of the present invention may include a standard solution of aqueous progesterone, or any other indicated steroid hormone, diluted with normal saline to achieve concentrations of 5 mg/ml to 0.5 μg/ml. The strength of a dilution selected for treatment may be based on a severity of the patient's symptoms and prior treatment history. This selection methodology may be similar to that used in treatments with foreign allergens and appropriate selections for an individual patient will be apparent to one skilled in the art.

Typically, 0.1 cc of a hormone dilution (0.5 mg–0.05 μg per dose) is administered sublingually every other day. The frequency of administration may be increased to every day or more often, as required, to achieve a desired treatment response. The strength of the hormone dilution selected for treatment may also be varied depending on severity of symptoms and on response achieved. Response to therapy may be measured on a 10-point point scale of symptom severity as reported by a patient to a clinical provider. Additional tests for abatement of symptoms may also be used. Treatment of hormone allergy symptoms may continue for months or years as indicated by each patient's clinical condition.

In an alternative embodiment of this invention, the dilution may be administered intradermally for instance, in patients who may have no response to sublingual drops or are unable to use the sublingual delivery method.

EXAMPLES

Example 1

Dilution Protocol

Progesterone USP 50 mg/ml (Schein Laboratories, Florham, N.J.) is diluted with physiologically-compatible(normal) saline to produce the progesterone dilutions used in treatments. The initial progesterone is suspended in sesame oil. Therefore, to achieve an even suspension, the vial must be vigorously shaken at each stage of the initial preparation and before use of each vial. The first dilution is made by adding 0.5 ml of progesterone to 4.5 ml normal saline. This results in a 1:10 dilution of progesterone (progesterone 5 mg/ml) which is labeled "PROG 1." After vigorously shaking the PROG 1 vial, 0.5 ml is withdrawn and injected into the next vial of 4.5 ml of normal saline. This results in a 1:100 dilution of Progesterone (0.5 mg/ml, "PROG 2"). To produce the next dilution, a vial of PROG 2 is immediately withdraw 0.5 ml and injected into the next vial of 4.5 ml of normal saline. This results in a 1:1000 dilution of Progesterone (50 μg/ml "PROG 3"). These steps are repeated until there are five serial dilutions labeled "PROG 1" through "PROG 5." (See Table 1). A milligram (mg) is defined as $\frac{1}{1000}$ or $10^{-3}$ of a gram. A microgram (μg) is defined as $\frac{1}{1,000,000}$ or $10^{-6}$ of a gram.

TABLE 1

| | Progesterone Dilutions | | |
| --- | --- | --- | --- |
| Label | Progesterone Concentration | Dilution | Dosage Used (.1 ml) |
| PROG 1 | 5 mg/ml | $10^{-1}$ | .5 mg |
| PROG 2 | .5 mg/ml | $10^{-2}$ | .05 mg |
| PROG 3 | 50 μg/ml | $10^{-3}$ | 5 μg |
| PROG 4 | 5 μg/ml | $10^{-4}$ | .5 μg |
| PROG 5 | .5 μg/ml | $10^{-5}$ | .05 μg |

Example 2

Treatment Protocol

Before beginning treatment, all of a patient's symptoms are assessed and assigned a numerical value by the patient, based on a 10-point scale. Drops are administered to a patient in a standard sequence, starting with plain normal saline (NS) to assess the placebo effect. After plain normal saline, PROG 5 is administered, followed by PROG 3, and then PROG 1.

After the drops are placed under a patient's tongue, the patient is instructed not to swallow for 5 seconds. Then the patient is asked to swallow the drops. After an additional 15 seconds, the patient is asked to note any change in any symptoms. The patient is questioned about each area of possible symptoms whether they are initially complained of or not. The question is always asked in the same manner, "Are your symptoms worse, unchanged, or better?" The question is asked in this way to always give the patient the option of selecting "worse" or "unchanged" before "better." This is designed to minimize the power of suggestion or "placebo" effect.

If all of the symptoms disappear completely after the placebo, the results are recorded and no further treatment is administered. If at any point, all the symptoms are relieved, the tests are concluded and the patient is provided with a vial with the same dilution of progesterone drops that relieved the symptoms. The patient is instructed to use the drops as often as needed. If symptom relief does not last 12–24 hours, this is an indication that the patient needs a vial one dilution stronger than what she is currently using.

Patients are questioned about each of twelve standard categories of discomfort (see Table 2). If patients are only asked generally to describe their symptoms they will often omit symptoms that are not included in their chief complaint but that they are experiencing concomitantly with the chief complaint. The patient is asked to grade the symptoms on a scale of 1 to 10. "Zero" is no symptoms at all and "ten" is the most intense discomfort the patient has experienced with a symptom.

TABLE 2

Standard Template for Recording Response to Progesterone Dilutions

| Symptom Location | Normal Saline | PROG 5 | PROG 3 | PROG 1 |
|---|---|---|---|---|
| Neck | | | | |
| Nose | | | | |
| Eyes | | | | |
| Throat | | | | |
| Shortness of Breath | | | | |
| Headache | | | | |
| Skin | | | | |
| Ears | | | | |
| Back | | | | |
| Hips | | | | |
| Lower Extremity | | | | |
| Upper Extremity | | | | |
| Other | | | | |

The symptoms in Table 2 are defined as follows: "neck" refers to musculoskeletal pain in the neck, "nose" refers to blockage or stuffiness in the nose, "eyes" refers to irritation such as burning or itching, "shortness of breath" is defined as a patient's perception of the inability to take a deep breath, "headache" refers to pain in the head region, "skin" is defined as itching, burning or a rash on the skin, "ears" refers to pain or pressure in the ears, "back," "hips," "lower extremity" and "upper extremity" all refer to pain in those areas including arthritis-type pain or pain from chronic or acute injury.

Example 3

Treatment Response

Data has been gathered on the clinical response to dilute progesterone therapy for over 300 patients. Patients presenting for treatment ranged in age from 30 to 70 years old and were predominantly female. See Table 3.

TABLE 3

Patient Demographics

| Age Range | 30–70 years |
|---|---|
| Male:Female | 1:4 |
| Progesterone Dosage | 0.5 mg–.05 µg |
| Length of Treatment | 1–90 days |

Patients generally responded favorably in the areas of both allergy and pain symptoms. In the area of allergy symptoms, 66–87% of patients responded depending on the site of allergy symptoms. See Table 4.

TABLE 4

Response to Treatment-Allergy Symptoms (N = 300)

| Site | # of Patients | Responders | % Improvement | % Responders |
|---|---|---|---|---|
| Nose | 109 | 89 | 63% | 82% |
| Eyes | 90 | 73 | 57% | 81% |
| Throat | 92 | 70 | 64% | 76% |
| Ear | 35 | 23 | 52% | 66% |
| Skin | 34 | 27 | 74% | 79% |
| Asthma/SOB | 142 | 124 | 67% | 87% |

In the area of pain symptoms, 72–92% of patients responded depending on site of pain symptoms. See Table 5. Over half of the total patients in both groups responded with symptom relief in excess of 60%.

TABLE 5

Response to Treatment-Pain Symptoms (N = 300)

| Site | No. of Patients | Responders | Percent Improvement | Percent Responders |
|---|---|---|---|---|
| Neck | 144 | 104 | 62% | 72% |
| Headache | 103 | 84 | 69% | 82% |
| Back | 57 | 57 | 72% | 82% |
| Hips | 26 | 24 | 79% | 92% |
| Arm | 61 | 48 | 76% | 79% |
| Leg | 50 | 40 | 75% | 80% |

Progesterone antibody levels (immunoglobulins-IgG and IgM) have also been measured (Immunosciences Lab, Beverly Hills, Calif.) and are higher than normal range in approximately 70% of patients before treatment.

Example 4

Improvement in Shortness of Breath

Figure 2A:
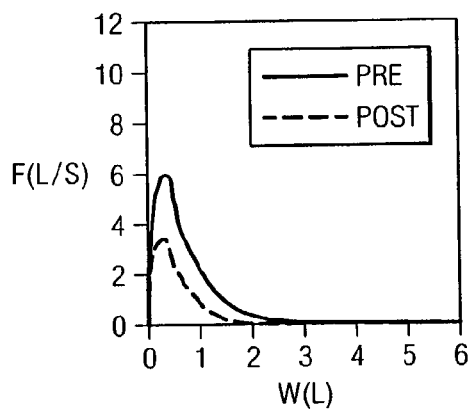
FIG. 2 illustrates spirometry results of a patient before and after treatment with a dilute steroid hormone composition incorporating teachings of the present invention.
Figure 2B:
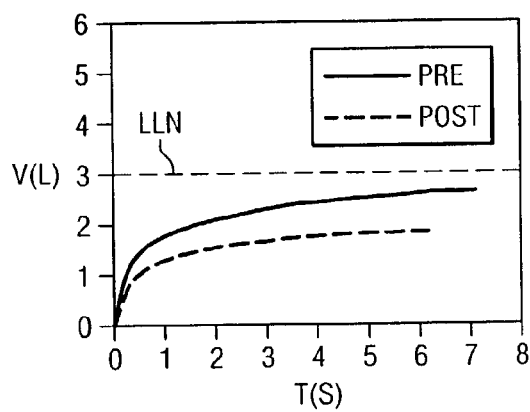

Spirometry was performed on 22 patients with shortness of breath who were treated with dilute progesterone drops. All 22 had improvement in spirometry with hormonal allergy treatment. An example of the improvement is shown in FIG. 2 which shows rate of air flow and lung volume in an individual patient pre- and post-treatment. Both the rate of air exchange (FIG. 2A, F(L/S)=air flow in liters per second) and the lung volume (FIG. 2B, V(L)=lung volume in liters, LLN=lower limits of normal for lung volume) of a female patient improved after dilute progesterone treatment in accordance with teachings of the present invention.

Although the present invention has been described with respect to specific preferred embodiments thereof, various changes and modifications may be suggested to one skilled in the art and it is intended that the present invention encompass such changes and modifications within the scope of the appended claims.

What is claimed is:

1. A method for treating at least one symptom of a hormone allergy, the method comprising:
   administering sublingually to a subject about 0.1 milliliter of a 0.05 milligram per milliliter estrogen dilution; and
   administering sublingually to the patient at least one additional estrogen dilution, wherein the at least one symptom is selected from the group consisting of shortness of breath, nasal congestion, eye irritation, and any combination and wherein relief of the at least one symptom occurs in about 20 seconds after the at least one additional estrogen dilution administration.

2. A method for treating at least one symptom of a hormone allergy comprising administering sublingually to a subject about 0.1 milliliter of a 0.05 milligram per milliliter testosterone dilution, wherein the at least one symptom is selected from the group consisting of shortness of breath, nasal congestion, eye irritation, and any combination thereof and wherein relief of the at least one symptom occurs in about 20 seconds after administration.

* * * * *